United States Patent [19]
Schneider

[11] 4,230,125
[45] Oct. 28, 1980

[54] METHOD AND APPARATUS FOR EFFECTING THE PROSPECTIVE FOREWARNING DIAGNOSIS OF SUDDEN BRAIN DEATH AND HEART DEATH AND OTHER BRAIN-HEART-BODY GROWTH MALADIES SUCH AS SCHIZOPHRENIA AND CANCER AND THE LIKE

[76] Inventor: Daniel E. Schneider, 61 E. 93rd St., New York, N.Y. 10028

[21] Appl. No.: 55,567

[22] Filed: Jul. 9, 1979

[51] Int. Cl.³ .............................................. A61B 5/04
[52] U.S. Cl. .................................... 128/670; 128/731
[58] Field of Search ............................... 128/670–672, 128/731

[56] References Cited
U.S. PATENT DOCUMENTS

| | | | |
|---|---|---|---|
| 3,706,308 | 12/1972 | John et al. | 128/670 |
| 3,814,082 | 6/1974 | Taylor | 128/670 |
| 3,850,161 | 11/1974 | Liss | 128/731 |
| 3,908,639 | 9/1975 | McIntyre | 128/672 |
| 4,092,981 | 6/1978 | Ertl | 128/731 |

FOREIGN PATENT DOCUMENTS 2531242 1/1976 Fed. Rep. of Germany .......... 128/670

Primary Examiner—William E. Kamm
Attorney, Agent, or Firm—Sprung, Felfe, Horn, Lynch & Kramer

[57] ABSTRACT

A method and apparatus for effecting the prospective forewarning diagnosis of sudden brain or heart death or other brain-heart and growth malady in a person comprises measuring the T-3 factor of the person, measuring the alpha frequency of the brain of a person as a function of the person's pulse rate, calculating the heart and brain weight as volume x specific gravity as a function of the alpha frequency, pulse and the T-3 factor and comparing the measured T-3 factor and the calculated heart and brain weight as volume x specific gravity to the normal values for the person's age. The deviation from the normal values is indicative of a prospective forewarning of sudden heart or brain death or other brain-heart and growth malady and effects the forewarning diagnosis thereof.

9 Claims, 5 Drawing Figures

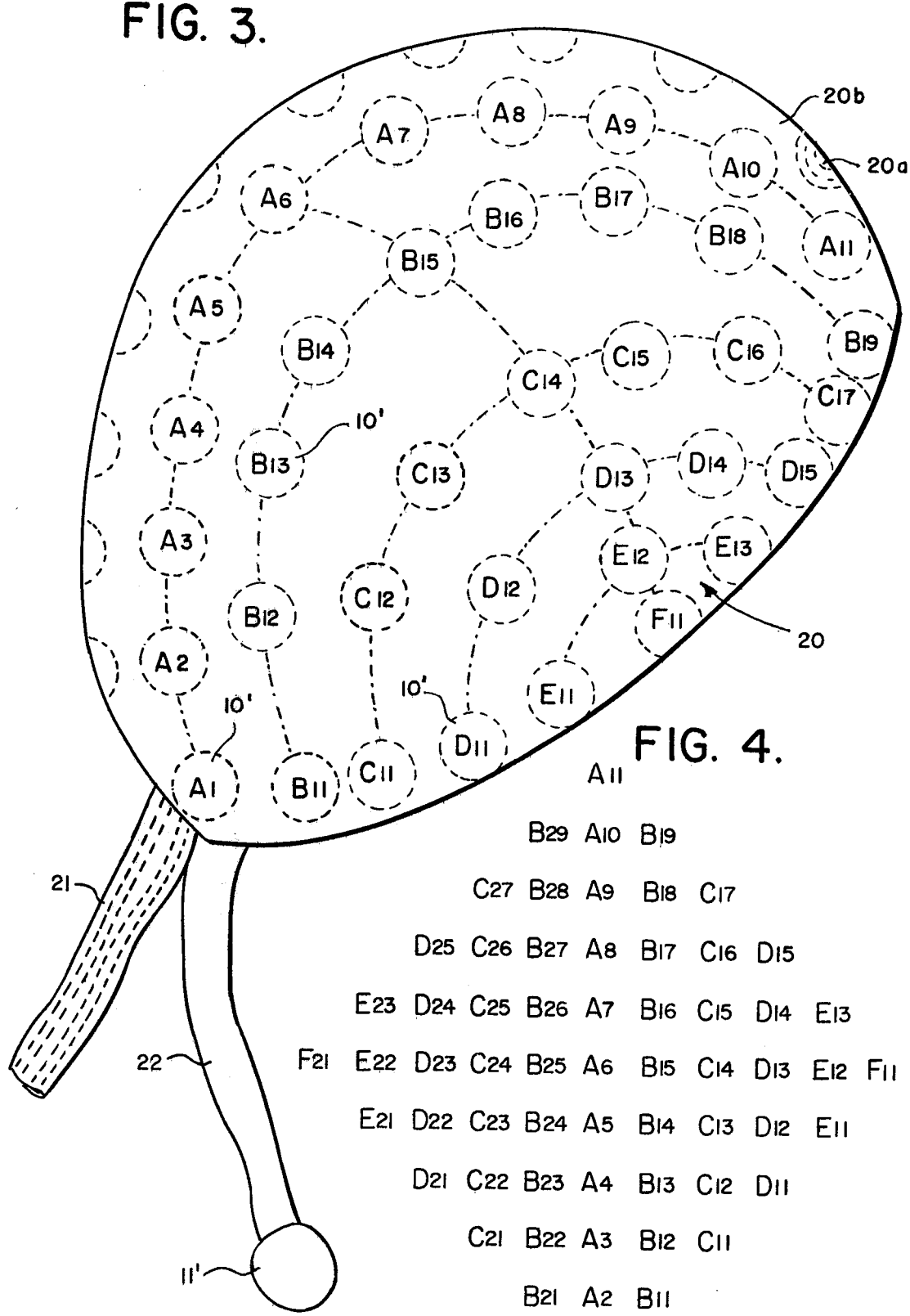

METHOD AND APPARATUS FOR EFFECTING THE PROSPECTIVE FOREWARNING DIAGNOSIS OF SUDDEN BRAIN DEATH AND HEART DEATH AND OTHER BRAIN-HEART-BODY GROWTH MALADIES SUCH AS SCHIZOPHRENIA AND CANCER AND THE LIKE

BACKGROUND OF THE INVENTION

The present invention relates to a method and apparatus for effecting the prospective forewarning diagnosis of sudden brain or sudden heart death, shock, heart attack or other brain-heart-body growth malady in a person.

Presently, techniques such as the electrocardiogram (EKG) and the electroencephalogram (EEG) are known for effecting diagnosis of brain and heart maladies in a person. However, neither of these techniques have any unquestionable forewarning capacities. They are largely retrospective and have proven largely to be "after-the-fact" instrumentations with respect especially to the forewarning diagnosis of sudden heart death, sudden brain death and either impending schizophrenia or impending or just beginning cancer.

SUMMARY OF THE INVENTION

The object of the present invention is to provide a prospective forewarning diagnosis of such brain and heart maladies as sudden brain-death, heart-death, impending schizophrenia or just beginning cancer in a person and thus eliminate the disadvantages of known techniques. This prospective forewarning diagnosis is achieved as a result of the use of heretofore unknown measurements, with which, when utilized in bioplasma equations that have been developed, one is able to measure critical volume changes in the brain and heart as "pulsing volumes" which are antecedent to sudden heart death and sudden brain death. Also with respect to cancer and schizophrenic syndromes, one is able to detect potentially critical changes in symmetry configurations which are indicative thereof.

It is the total process and apparatus of the present invention which has the ability to produce measurements which when processed by the diagnostician preferably with the aid of computing apparatus can theoretically effect the prospective forewarning diagnosis of sudden heart death, sudden brain death and stroke, including brain distortions caused by brain tumors, oncoming schizophrenia and the first brain-body evidences of cancer.

The total process and apparatus of the present invention greatly enhances the present EEG and EKG techniques and utilizes a novel use of circuitry and instrumentation. The new instrumental approach, while similar to that used for the EEG and EKG, is actually distinctly different and entirely original in its fundamental theory and application. It searches out hitherto unrecognized distortions of the brain and heart as "pulsing volumes" dynamically inseparable and essential to the life-process itself.

This and other objects of the present invention are achieved by the method and apparatus of the present invention which can be better understood with reference to the foregoing detailed description thereof and the accompanying drawings wherein:

BRIEF DESCRIPTION OF THE DRAWINGS

FIG. 3 is a partially sectioned side view of another embodiment of the present invention;

FIG. 4 depicts in schematic form the electrode grid of the apparatus of FIG. 3.

DESCRIPTION

The specific and unique feature of the QREEG tracing is that it permits the calibration of the voltage of the EEG tracing in a relationship to the voltage of the QR tracing. This is not possible with present day EEG or EKG systems. Since this voltage factor is extremely important in heart attack, the QREEG tracing adds a uniquely forewarning potentiality. By superimposing the QREEG tracing upon the existing electrocardiogram, one can identify regularly that alpha wave of the EEG which corresponds to the P wave and the T waves of the EKG. This makes possible significant relationships between voltage and pacing factors not otherwise obtainable.

Figure 1:
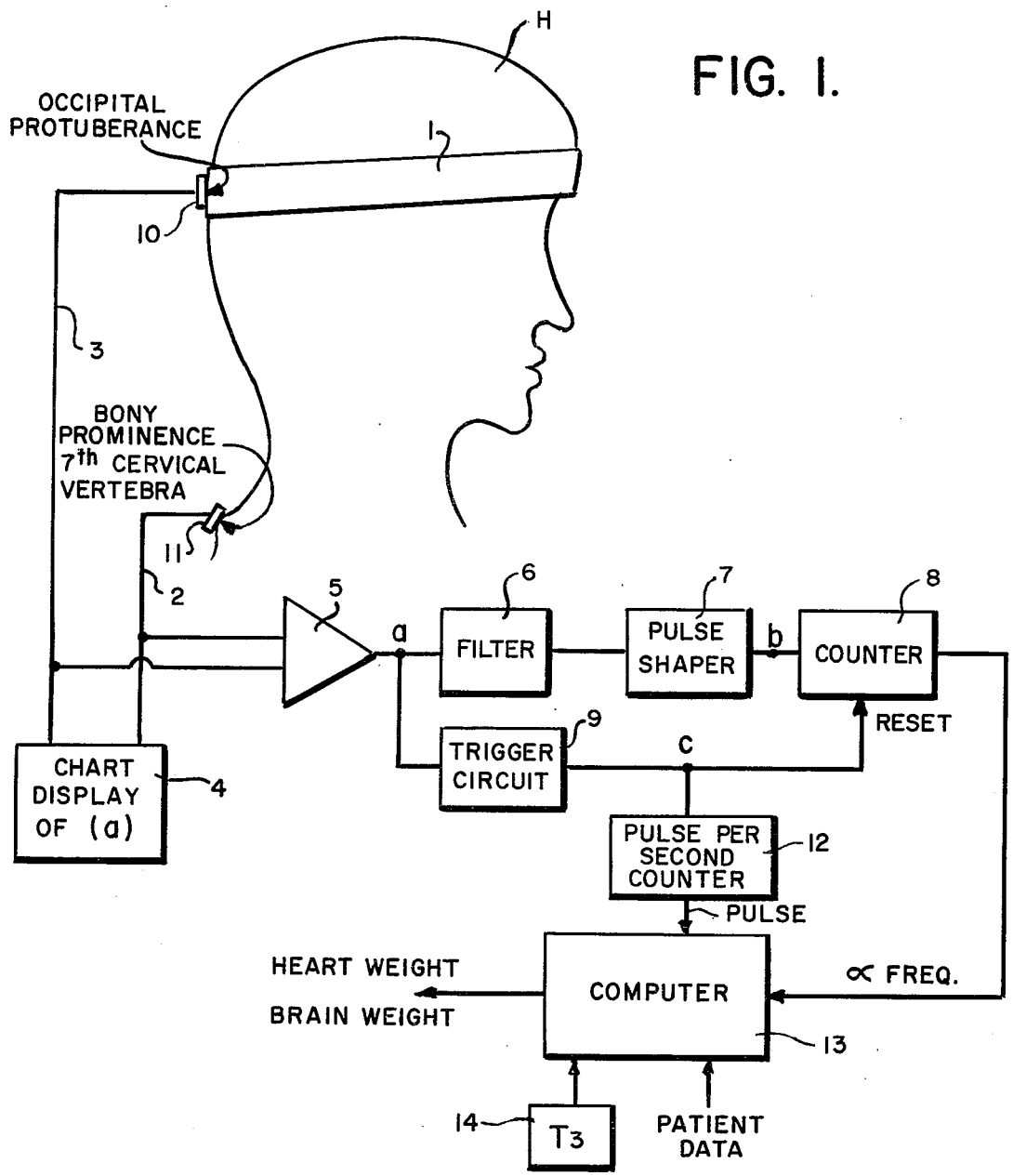
FIG. 1 is a schematic representation of the apparatus of one embodiment of the present invention.
Figure 2:
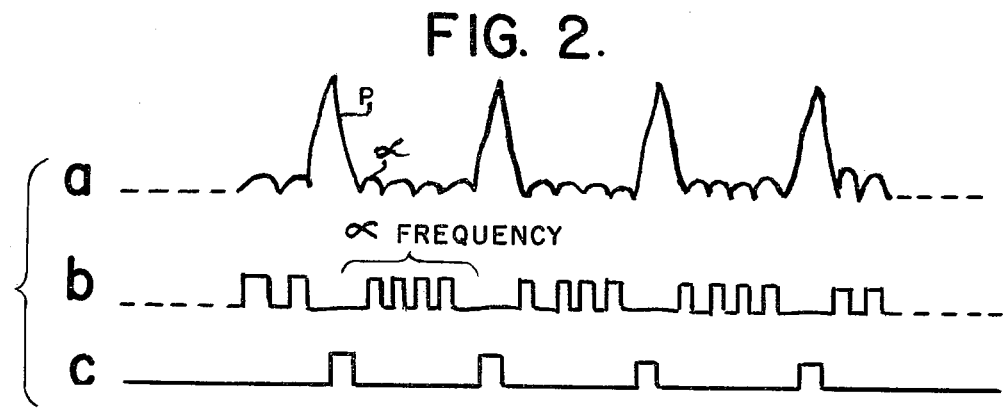
FIG. 2 shows the signal wave forms for the signals generated in the apparatus of FIG. 1.

Referring now to FIGS. 1 and 2, the basic embodiment of the method and apparatus of the present invention is depicted.

The embodiment shown is a basic two electrode embodiment utilizing electrode 10 which is disposed over the occipital proturberance and electrode 11 which is disposed over the bony prominence of the seventh cervical vertebra. By placing the electrodes 10, 11 thusly, and connecting the electrodes 10 and 11 via leads 3 and 2 respectively to a chart display device 4 such as an EEG machine, a tracing is obtained which "paces" the relationship between the bio-electrical impulses known as "brain waves" and the variations therein made by the brain glia acting as "dynamic ligatures" between the great arteries of the brain and the brain's perceiving-recording-motivating-motor controlling neurons. This pulse appearing in "brain-waves" (EEG electrical tracings) is believed to be not merely a "transfer" from the EKG, but rather the piezoelectric impact of the glial "bridge" from the glial "footplate" on brain arteries to the neurons. The heart pulse in the EEG tracings obtained by the method of the invention corresponds to and is practically simultaneous with the QR segment of the EKG which records the major electrical activity of the pulsing ventricles together with the EKG's S and T waves. The result, which is shown in FIG. 2 as signal "a", is merely the same as the output of amplifier 5, which produces the output signal "a" as a function of the two signals with respect to one another and is called the "QREEG" tracing since it appears as if it were a combination of the QR segment of the EKG and the EEG tracing, though actually it is a measurable phenomenon quite distinct from either the EEG and/or the EKG alone.

What is obtained in the output of the chart display of signal "a" is the so-called alpha ($\alpha$) frequency, which is the number of alpha pulses per pulse P, where the number of pulses P per second is equivalent to the pulse rate of the person under test. This alpha frequency is utilized as will be hereinafter explained.

The purpose of the method and the apparatus of the present invention is to measure the brain volume and heart volume of the person under test to obtain the brain and heart weight where for a known specific gravity, weight=volume×specific gravity). This is done by utilizing the following bioplasma equations which enable one to determine the brain and heart weight as volume×specific gravity, at any time in life from birth onward. These are unique bioplasma equations of critical "pulsing volumes" applicable to forewarning capabilities against sudden heart death and brain death since as noted the heart weight and brain weight are based upon volume times specific gravity, both the heart and brain pulsing unseparably and characteristically during the normal life-process, in critical ratio to each other.

The equations are as follows:

Heart Weight (vol. × sp. gr.) =

$$\sqrt{\frac{\text{Body vol.} \times \text{sp. gr.}_{t_n} \times 4.92/T\text{-3 Factor}}{2.8026 \times 10^2 \times \left[\frac{\text{Pulse} + \text{Gender Force Factor}}{\text{Pulse} \times \text{alpha EEG frequency}}\right]}}$$

Brain Weight (vol. × sp. gr.) =

$$\sqrt{\frac{\text{Body vol.} \times \text{sp. gr.}_{t_n} \times \left[\frac{4.92}{T\text{-3 factor}}\right] \times [(T\text{-3 factor})^2]}{2.8026 \times 10^2 \times \left[\frac{\text{Pulse} + \text{Gender Force factor}}{\text{Pulse} \times \text{alpha EEG frequency}}\right]}}$$

It must be stressed that these equations have never been derived before or used in any theory or any instrumentation. They are the unique, original result of equating Bioplasma Equation I to Bioplasma Equation II as set forth in the book "Revolution in the Body Mind, Vol. I", on pages 33 and 34, by Daniel E. Schneider, Alexa Press.

An important factor original to the QREEG process in both of the equations above is the presence of the T-3 factor which refers to the critical tri-iodothyronine utilization by brain, heart and body and is here for the first time shown to be practically directly proporational to the ratio of brain weight to heart weight as pulsing volumes at any age after birth.

In the above equations, $t_n$ means at any time and the T-3 variable is also implicitly taken to mean at the time of the use of the method and apparatus. The person's pulse is taken to be per second at the time of testing and the alpha frequency and gender force factor are also determined at the time of testing.

The T-3 factor is a well-known parameter of "basal metabolism" which is body-heart-brain energy utilization per kilo body weight and the testing therefor is a well-known concept and will not be gone into in any greater detail.

The foregoing Table I shows the heart and the brain as the pulsing volumes in relation to the body as a pulsing volume, with all three, brain, heart and body pulsing in relation to heart pulse, brain wave and gender force factor. With the recognition that the variable of the brain to heart ratio is practically equivalent to the T-3 factor of human metabolism per kilogram, Table I shows the "standard or normal values" for persons at various ages for heart weight and brain weight as pulsing volumes.

As can be seen from Table II the brain to heart ratios of growth are a function of the T-3 factor and the limb and torso shaping ratios of gender growth are a function of the T-4 factor which is another well known and conventional diagnostic parameter. In this manner, the QREEG process establishes the original discovery that the brain to heart ratios and the gender shaping ratios comprise the hitherto unattainable solution to the problem of the peculiar curve of basal metabolism (brain-body-heart oxygen utilization) per kilogram per year.

The tables show that the results of the two equations are extremely accurate with respect to normal heart and brain weights.

As shown in FIG. 1, the signal obtained at the output of amplifier 5 is filtered by filter 6 to obtain only the relatively higher frequency alpha wave forms and pulse shaper 7 pulse shapes these alpha wave forms into square waves which can be utilized by digital circuitry. These alpha waves are shown as signal "b" in FIG. 2. Simultaneously, trigger circuit 9 triggers on the relatively higher amplitude P pulses to produce an output wave form "c" shown in FIG. 2. Output wave forms "b" and "c" are utilized by counter 8 to count the alpha frequency per each pulse in "c" and pulse counter 12 is utilized to count the number of pulses of signal "c" per second in order to obtain the actual patient pulse. The outputs of counters 8 and 12 are thereafter fed into a computer 13 which also receives the fixed patient data such as body weight, etc., utilized in the above-referenced equations, and the input of the T-3 factor which has been measured at that time by known measuring device shown as 14. The computer is then simply programmed to calculate the heart weight and brain weight as a function of the body volume×specific gravity, the T-3 factor, the alpha frequency and the pulse and the other fixed patient data as set forth in the equations. These calculations are simple to obtain and require no special computer hardware or more than the simplest computer program.

TABLE I

SHOWING THE HEART AND THE BRAIN AS PULSING VOLUMES IN RELATION TO THE BODY AS A PULSING VOLUME — ALL THREE: BRAIN, HEART AND BODY PULSING IN RELATION TO (1) HEART PULSE (2) BRAIN WAVE (3) GENDER FORCE FACTOR. — OBTAINED BY EQUATING THE EQUATIONS I AND II OF THE BIOPLASMA CONCEPT WITH THE DISCOVERY OF THE VARIABLE OF BRAIN/HEART RATIO AS PRACTICALLY EQUIVALENT TO THE T-3 COMPONENT OF HUMAN METABOLISM PER KILO. (BODY VOLUME AS STATED IN TABLE II OF THE BIOPLASMA EQUATIONS IN THE BOOK "REVOLUTION IN THE BODY-MIND", VOL. I, pg. 38)

| AGE (yrs.) | (1) BODY VOL.(cc.) × specific grav. × 4.92/Brain-Heart* Ratio = Numerator | (2) NUMERATOR per Oscillation Ratio | (3) SQUARE ROOT of Col. (2) = Heart gms. | (4) (COL. 2) × (Brain/Heart*)$^2$ | (5) SQUARE ROOT of Col. (4) = Brain gms. |
|---|---|---|---|---|---|
| | 67033.25 | 21144.609/ | 590.8795 | | |

TABLE I-continued

SHOWING THE HEART AND THE BRAIN AS PULSING VOLUMES IN RELATION TO THE BODY AS A PULSING VOLUME — ALL THREE: BRAIN, HEART AND BODY PULSING IN RELATION TO (1) HEART PULSE (2) BRAIN WAVE (3) GENDER FORCE FACTOR. — OBTAINED BY EQUATING THE EQUATIONS I AND II OF THE BIOPLASMA CONCEPT WITH THE DISCOVERY OF THE VARIABLE OF BRAIN/HEART RATIO AS PRACTICALLY EQUIVALENT TO THE T-3 COMPONENT OF HUMAN METABOLISM PER KILO. (BODY VOLUME AS STATED IN TABLE II OF THE BIOPLASMA EQUATIONS IN THE BOOK "REVOLUTION IN THE BODY-MIND", VOL. I, pg. 38)

| AGE (yrs.) | (1) BODY VOL.(cc.) × specific grav. × 4.92/Brain-Heart* Ratio = Numerator | (2) NUMERATOR per Oscillation Ratio | (3) SQUARE ROOT of Col. (2) = Heart gms. | (4) (COL. 2) × (Brain/Heart*)$^2$ | (5) SQUARE ROOT of Col. (4) = Brain gms. |
|---|---|---|---|---|---|
| Birth | × 1.000934<br>× 0.3151403<br>= 21144.609 | 35.784976<br>= 590.8795 | 24.308013 | × (15.6121)$^2$<br>= 144019.61 | 379.4992 |
| ½ | 149168.21<br>× 0.9989498<br>× 0.2312623<br>= 34460.753 | 34460.753/<br>29.58343<br>= 1164.8667 | 34.130143 | 1164.8667<br>× (21.2745)$^2$<br>= 527223.72 | 726.1018 |
| 1 | 218253.09<br>× 0.9983555<br>× 0.2392784<br>= 52137.368 | 52137.368/<br>26.965127<br>= 1933.5109 | 43.971705 | 1933.5109<br>× (20.5618)$^2$<br>= 817464.43 | 904.1374 |
| 2 | 345505.19<br>× 0.9988235<br>× 0.2835446<br>= 97850.872 | 97850.872/<br>29.0382<br>= 3369.7292 | 58.049368 | 3369.7292<br>× (17.3518)$^2$<br>= 1014574.9 | 1007.26 |
| 3 | 462667.81<br>× 1.0006686<br>× 0.2905382<br>= 134512.54 | 134512.54/<br>30.74034<br>= 4375.7651 | 66.149556 | 4375.7651<br>× (16.9341)$^2$<br>= 1254810.5 | 1120.18 |
| 4 | 577164.41<br>× 1.0013087<br>× 0.3374156<br>= 194999.13 | 194999.13/<br>30.884142<br>= 6313.8917 | 79.460000 | 6313.8917<br>× (14.5814)$^2$<br>= 1342441.9 | 1158.6379 |
| 6 | 832168.26<br>× 0.9969922<br>× 0.4139481<br>= 343438.35 | 343438.35/<br>31.293679<br>= 10974.687 | 104.76014 | 10974.687<br>× (11.8855)$^2$<br>= 1550340.3 | 1245.1266 |
| 8 | 1124003.6<br>× 1.0011715<br>× 0.5193275<br>= 584409.77 | 584409.77/<br>32.771872<br>= 17832.663 | 133.53899 | 17832.663<br>× (9.4738)$^2$<br>= 1600533.2 | 1265.1218 |
| 10 | 1420193.6<br>× 0.9990661<br>× 0.5955469<br>= 845001.96 | 845001.96/<br>33.567749<br>= 25173.03 | 158.6601 | 25173.03<br>× (8.2613)$^2$<br>= 1718036.6 | 1310.7389 |
| 12 | 1744622.6<br>× 1.0025611<br>× 0.6401695<br>= 1119714.5 | 1119714.5/<br>36.553627<br>= 30632.103 | 175.02029 | 30632.103<br>× (7.6833)$^2$<br>= 1808307.9 | 1344.7333 |
| 15 | 2336709.2<br>× 1.0038975<br>× 0.9120362<br>= 2139469.5 | 2139469.5/<br>34.399155<br>= 62195.408 | 249.39007 | 62195.408<br>× (5.3945)$^2$<br>= 1809925.5 | 1345.3347 |
| 18 | 2796551.8<br>× 0.9951144<br>× 1.000000<br>= 2782888.9 | 2782888.9<br>37.225645<br>= 74757.306 | 273.41782 | 74757.306<br>× (4.92)$^2$<br>= 1809605.2 | 1345.2156 |

*NOTE:
Brain-Heart Ratio is Equal, as stated, in text, to the T-3 factor.

TABLE II

Showing the Brain-Heart Ratios of Growth As Functions of T-3(Tri-iodothyronine) and The Shaping Ratios of Gender Growth or (d)L/(d)W as Functions of T-4 (Tetra-iodothyronine) In Which The Brain-Heart Ratios and the Gender Shaping Ratios Solve the Problem of the Peculiar Curve of Metabolism/Kg./Yr.

| Age (yrs.) | Brain-Heart (T-3) | $(Brain-Heart)^2$ 18 years + *Brain-Heart 18 years or $24.2064 + 1.000 = 25.2064$ | $\frac{(d)L}{(d)W(Freq. + t)}$** + **[Q.1 alpha freq. + $(0.1t)^2$] | Calories per kilo per year | Total Heat × Body Wt. (Kgs.) |
|---|---|---|---|---|---|
| Birth | 15.62 | + 25.2064 + zero | — | =40.8264 × 3.44 | =140.4428 |
| ½ | 21.27 | + 25.2064 | +10.47159 | =56.9480 × 7.56 | =430.5269 |
| 1 | 20.56 | + 25.2064 | +14.8320 | =60.5984 × 10.06 | =609.6199 |
| 2 | 17.35 | + 25.2064 | +10.1325 | =52.6889 × 12.48 | =657.5575 |
| 3 | 16.93 | + 25.2064 | +5.6786 | =47.8150 ×14.711 | =703.4065 |
| 4 | 14.58 | + 25.2064 | +6.6952 | =46.4816 × 16.74 | =778.1020 |
| 6 | 11.88 | + 25.2064 | +3.6153 | =40.7017 × 21.556 | =877.3658 |
| 8 | 9.47 | + 25.2064 | +2.4547 | =37.1311 × 26.867 | =997.6013 |
| 10 | 8.26 | + 25.2064 | — | =33.4664 ×32.63 | =1092.0086 |
| 12 | 7.76 | + 25.2064 | — | =32.9664 × 38.996 | =1285.5577 |
| 15 | 5.39 | + 25.2064 | — | =30.5964 × 52.30 | =1600.1917 |
| 18 | 4.92 | + 25.2064 | — | =30.1264 × 61.5556 | =1854.4606 |

*The Brain-Heart Ratio For Heart Maintenance is 4.92/4.92 = 1.0000.
The Brain-Heart Ratio For Brain Maintenance is $(4.92)^2 = 24.2064$, and the sum of both = 25.2064 as shown in the second column.

FIG. 1 shows the electrode 10 being disposed at the occipital protuberance by an elastic headband 1, and while it is desirable to take a reading at this portion of the head, it is also desirable to take further readings at other portions of the head which are above the surface area of the brain. This can be carried out by taking the aforesaid readings with the electrodes in place as shown in FIG. 1 and thereafter moving electrode 10 to various discrete positions on the top of the head above the brain.

Figure 5:
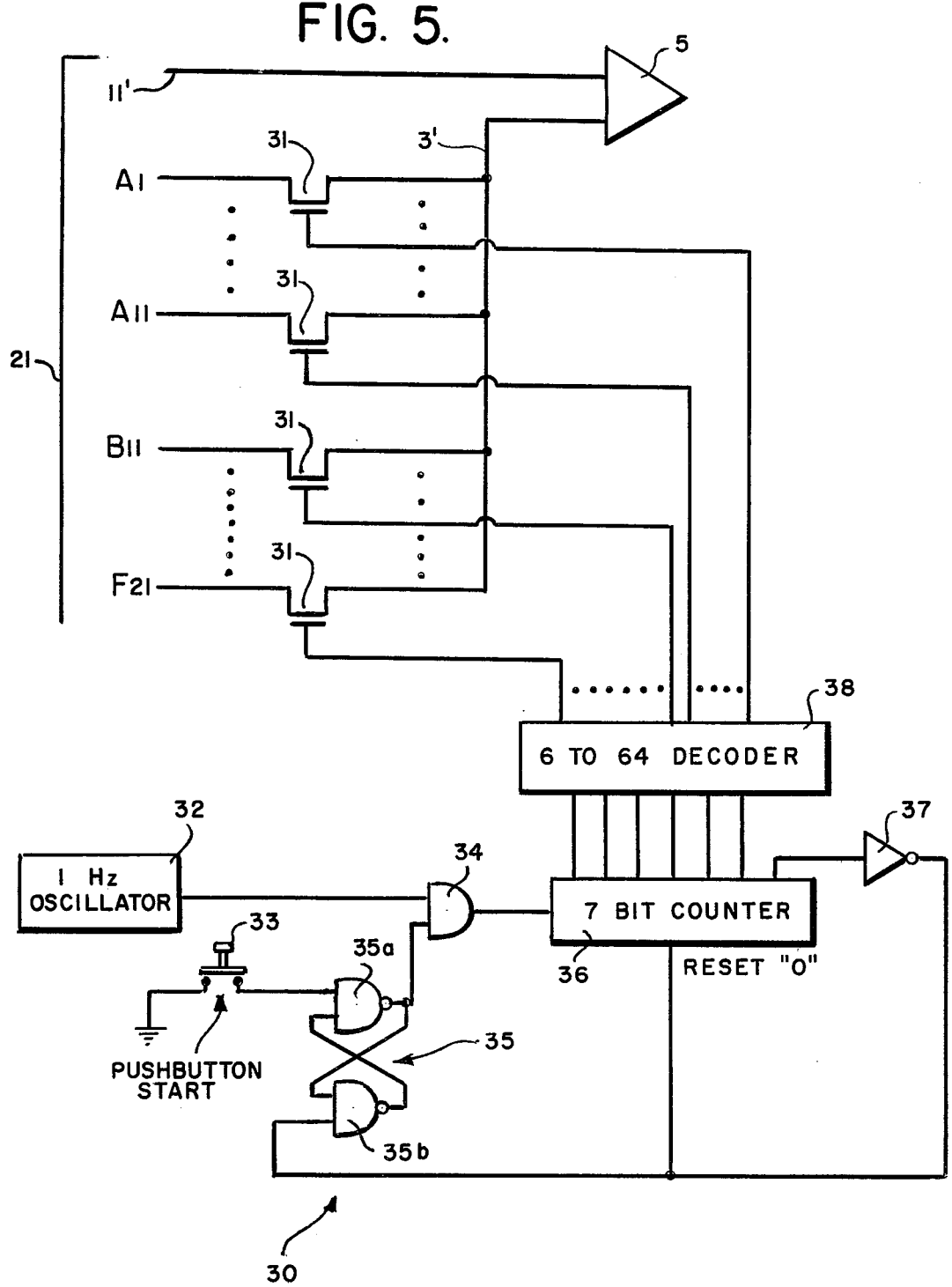
FIG. 5 is a schematic of electrical circuitry for effecting the operation of the embodiment shown in FIG. 3.

FIGS. 3-5 show a second embodiment which provides means for automatically carrying out these multiple readings without the necessity of manually moving electrode 10 from one position to the other on the head.

As shown in FIG. 3, a support means for a plurality of electrodes 10' is shown including an elastic cap 20 having an inner elastic layer 20a on whose inner surface is disposed a plurality of electrodes 10' numbered for convenience $A_1-F_{21}$ and an outer elastic member 20b which coverss the wires extending outwardly from each electrode and forming part of the wire bundle 21. In the embodiment shown, 61 electrodes 10' are used in addition to electrode 11' which corresponds to that which is placed at or around the bony prominence of the seventh cervical vertebra and which is connected to the cap 20 via a flexible connecting member 22 which enables the electrode 11' to be placed in the proper position when the cap 20 is placed on the head of the person being tested.

FIG. 4 shows a simplified layout of the electrodes in their positions relative to one another and the use of this layout will be described hereinafter.

The bundle of 62 wires 21 is then fed into the circuitry shown in FIG. 5 for providing an analogue multiplexing of the signals obtained from the 61 electrodes 10'. In the embodiment shown, for the sake of ease of representation, sixty-one electrodes 10' are utilized, however, it should be recognized that any practical number of electrodes can be used taking into account the ultimate cost of the device and space limitations for the electrodes on the supporting means.

For the given embodiment, the multiplexing is carried out by sixty-one analogue FET switching elements 31 whose inputs are each attached to one of the output signals from the electrodes 10' and whose outputs are all interconnected. The gate or control inputs of the switching elements 31 are individually connected to outputs of a 6 to 64 decoder 38 which receives its input from 6 bits of a 7-bit counter 36. The counter 36 is stepped via a 1 hertz oscillator 32 whose clock signal is controlled via flipflop 35, AND gate 34 and inverter 37. When a pushbutton 33 is depressed, set-reset flipflop 35 which comprises MAND gates 35a and 35b is set, thereby enabling AND gate 34 to permit oscillator 32 to clock the counter 36 and effect its counting. For each count in the counter 36, an individual one of the FET gates of elements 31 is enabled which puts the signal from the associated electrode 10' at the input of amplifier 5 along with the signal from electrode 11'. It is believed that a sampling of this signal from the two electrodes relative to one another need only be anywhere from one-half of a second to one minute and thus, in the embodiment shown, each signal "a" lasts for one second as a result of the 1 Hz frequency of the oscillator 32. Each signal emanating from amplifier 5 is fed into the computer 13 as set forth hereinabove and the computer 13 can compute the various values of heart weight and brain weight (as volume × specific growth) for each signal received therein by triggering the computer with the oscillator 32 such that it is aware that a new data input is being received each second.

Upon the counting of sixty-four counts, of which three are not utilized in this embodiment, the seventh bit becomes a "one" which enables inverter 37 to reset flipflop 35 thus preventing any pulses from oscillator 32 from reaching the counter 36 and to also reset the counter back to count zero. At this time, the reset signal for flipflop 35 is also removed and thus enables the flipflop 35 to be set again upon the depression of pushbutton 33.

Because of the capacity of modern day computers for data processing, it is possible by simple programming techniques to have the data fed in from all of the sixty-one electrodes 10' to be processed and have the brain weight and heart weight and the ratio of brain weight to heart weight calculated and these three values printed out at the locations corresponding to the positioning of the individual associated electrodes as shown in FIG. 4. This can then be used as a diagnostic tool to give the diagnostician the ability to see the changes in these values relative to the positions of the electrodes 10' and thus make visual correlations between the data without further requests of more sophisticated data processing by the computer.

The printout of the data in the configuration shown in FIG. 4 also aids in the determination of a disturbance of the symmetry of the QREEG brain field for the prospective forewarning diagnosis of cancer and schizophrenia in a person.

Since it has been found that the gravitational interaction equation given below illustrates the principle of the mirror-image symmetry and cell division and in the formation of the double heli as was postulated on pages 101–102 of Revolution in the Body-Mind Vol. I: Forewarning Cancer Dreams and the Bioplasma Concept by Daniel E. Schneider, Alexa Press, 1977, the grid shown in FIG. 4 and the values printed in this grid format, will reveal any changes in brain-body symmetry and thus forewarn the diagnostician of impending cancer or schizophrenia which would enable the diagnostician to run further tests to confirm such a diagnosis.

$$\frac{(13.59894 \text{ ergs})}{\text{gm}} \frac{(\text{Body Weight}^{\frac{1}{3}} \text{ gms} \times \text{Body Weight}^{\frac{1}{3}} \text{ gms})}{(\text{radius})^2} = \text{radius} \times \text{Pulse Freq. ergs/cms}$$

The method and the apparatus of the present invention aid the diagnostician in providing a forewarning of heart and brain maladies so as to justify further testing to confirm this forewarning. Key to the prospective forewarning diagnosis is firstly the deviation of the T-3 factor from the normal value for a given age, since this indicates a priori that there is an imbalance in the brain-heart-body symmetry. The calculation of the brain and heart weight individually and the deviation thereof from the normal values given in the above-listed tables, will then indicate to the diagnostician what is taking place in the patent. For example, if the T-3 factor is higher than normal, and the brain weight is up while the heart weight is normal, this will indicate the possibility of an impending stroke. Likewise, if the brain weight is normal and the heart weight is decreased, this will indicate the threat of a prospective heart attack. On the other hand, if the T-3 factor is lower than normal, and the brain weight is normal and the heart weight is increased, this may indicate an impending high blood pressure condition. If the brain weight is down while the heart weight is normal, this will indicate severe brain trauma or severe senile deterioration or damage. This latter is a highly infrequent situation except in very advanced age or else in known brain-deterioration such as Alzheimer's Disease, or other forms of brain atrophy.

What is claimed is:

1. A method for effecting the prospective forewarning diagnosis of sudden brain or heart death or other brain-heart and growth malady in a person comprising the steps of:
    measuring the T-3 factor of the person;
    measuring the alpha frequency of the brain of a person as a function of the person's pulse rate;
    calculating the heart and brain weight as volume × specific gravity as a function of the alpha frequency, pulse and the T-3 factor; and
    comparing the measured T-3 factor and the calculated heart and brain weight as volume × specific gravity to the normal values for the person's age; whereby the deviation from the normal values is indicative of a prospective forewarning of sudden heart or brain death or other brain-heart and growth malady and effects the forewarning diagnosis thereof.

2. The method according to claim 1, wherein the step of measuring the alpha frequency comprises placing a first electrode at or around the bony prominence of the seventh cervical vertebra and at least one second electrode on the head in the area above the brain and detecting the two signals therefrom relative to each other.

3. The method according to claim 2, wherein one second electrode is placed at the occipital protuberance.

4. The method according to claim 3, wherein the step of measuring the alpha frequency comprises placing a plurality of second electrodes on the head and successively detecting the two signals from the first electrode and each second electrode relative to that of the first electrode.

5. An apparatus for effecting the prospective forewarning diagnosis of sudden brain or heart death or other brain-heart and growth malady in a person, comprising:
    means for measuring the alpha frequency of the brain of a person as a function of the person's pulse rate;
    means receptive of the output of the measuring means and the measured T-3 factor and pulse for the person for calculating the heart and brain weights as a volume × specific gravity for the person as a function of the alpha frequency, T-3 factor and pulse; and
    means for displaying the calculated values;
    whereby the deviation of the measured T-3 factor from the normal value for the person's age in conjunction with the deviation of the calculated heart and brain weight as volumes × specific gravity from the normal values thereof for the person's age is indicative of a prospective forewarning sudden heart or brain death or other brain-heart and growth malady and effects the diagnosis thereof.

6. The apparatus according to claim 5, wherein the means for measuring the alpha frequency comprises a first electrode for disposing at or around the bony prominence of the seventh cervical vertebra and at least one second electrode for disposing on the head in the area above the brain and means for detecting the signals therefrom relative to each other.

7. The apparatus according to claim 6, wherein the means for measuring the alpha frequency comprises a plurality of second electrodes, support means receptive of the upper portion of the head and having an inner surface having the plurality of second electrodes disposed thereon for positioning the electrodes on the head in the area above the brain when the head is received therein and means for connecting the first electrode to the support means to enable the positioning thereof when the head is received in the support means.

8. The apparatus according to claim 7, wherein the means for detecting comprises means for detecting the signal from the first electrode and for successively detecting the signals from each second electrode relative to that from the first electrode.

9. The apparatus according to claim 6 or 8 wherein the means for calculating comprises a computer receptive of the output of the means for detecting.

* * * * *